United States Patent [19]

Imai et al.

[11] Patent Number: 4,886,928

[45] Date of Patent: Dec. 12, 1989

[54] HYDROCARBON DEHYDROGENATION PROCESS

[75] Inventors: Tamotsu Imai, Mt. Prospect; Robert J. Schmidt, Rolling Meadows, both of Ill.

[73] Assignee: UOP, Des Plaines, Ill.

[21] Appl. No.: 249,057

[22] Filed: Sep. 26, 1988

[51] Int. Cl.$^4$ .................... C07C 5/333; C07C 4/02; C07C 2/64

[52] U.S. Cl. .................... 585/660; 585/442; 585/444; 585/661

[58] Field of Search ............... 585/442, 444, 660, 661

[56] References Cited

U.S. PATENT DOCUMENTS

| | | | |
|---|---|---|---|
| 3,839,225 | 10/1974 | Acres | 252/432 |
| 4,003,826 | 1/1977 | Antos | 208/139 |
| 4,039,477 | 8/1977 | Engelhard et al. | 252/441 |
| 4,227,993 | 10/1980 | Engelhard et al. | 208/139 |
| 4,551,574 | 11/1985 | Imai et al. | 585/660 |
| 4,565,898 | 1/1986 | O'Hara et al. | 585/661 |

Primary Examiner—Curtis R. Davis
Attorney, Agent, or Firm—Thomas K. McBride; John F. Spears, Jr.

[57] ABSTRACT

A novel dehydrogenation process is disclosed which utilizes a catalyst comprising a platinum group component, a component selected from the group comprising scandium, yttrium, lanthanum, and actinium, a component selected from the group comprising tin, lead, and germanium, less than 0.3 wt. % of a halogen component, and an optional Group IA or IIA component, all on a refractory inorganic oxide support.

16 Claims, No Drawings

HYDROCARBON DEHYDROGENATION PROCESS

BACKGROUND OF THE INVENTION

This invention relates to the conversion of hydrocarbons, especially the dehydrogenation of dehydrogenatable hydrocarbons, in the presence of a catalytic composite.

The dehydrogenation of hydrocarbons is an important commercial process. This is because of the great demand for dehydrogenated hydrocarbons for industrial processes and products. For example, dehydrogenated hydrocarbons are utilized in the manufacture of various products such as detergents, high octane gasolines, and pharmaceutical products. Plastics and synthetic rubbers are other products which may be produced through use of dehydrogenated hydrocarbons. One example of a specific dehydrogenation process is dehydrogenating isobutane to produce isobutylene which may then be polymerized to provide tackifying agents for adhesives, viscosity-index additives for motor oils, and impact-resistant and anti-oxidant additives for plastics.

INFORMATION DISCLOSURE

U.S. Pat. No. 3,839,225 discloses a catalyst comprising oxides of scandium, yttrium, or the lanthanides along with platinum or rhodium and an optional base metal component selected from elements including tin and lead. All of the metals are located on an inert support. However, the catalyst disclosed is described as being most useful in the catalytic conversion of exhaust gases and not in a hydrocarbon dehydrogenation process.

U.S. Pat. No. 4,003,826 discloses a hydrocarbon conversion process utilizing an acidic catalyst comprising a platinum group metal component, a lead, or tin component, a halogen and a lanthanide series component. The catalyst of the instant dehydrogenation process is similar to the catalyst utilized in the '826 patent except the instant catalyst does not comprise a lanthanide series metal component.

U.S. Pat. No. 4,227,993 discloses a hydrotreating or hydroreforming process utilizing a catalyst composition comprising a platinum group metal, tin, and at least one metal selected from the group consisting of scandium, yttrium, thorium, and uranium. The catalyst composite also comprises a halogen component. The catalyst claimed as useful in the process of the '993 patent is similar to that of the instant invention. However, the hydrocarbon conversion process in which the catalyst of the '993 process is useful is catalytic reforming and not dehydrogenation.

U.S. Pat. No. 4,039,477 describes the catalyst composition of matter useful in the '993 process. Additionally, the catalyst is described as being useful for hydrocarbon dehydrogenation. However, the catalyst of the process of the instant invention may contain a Group IA or IIA element of the Periodic Table of the Elements. In addition, since the process of the instant invention is operated with a steam co-feed, the halogen component of the original catalyst formulation is stripped off the catalyst during normal operation and therefore the catalyst of the instant process will typically contain a very small amount of a halogen component during normal operations. Finally, the '477 patent does not mention the utility of such a catalyst in a dehydrogenation process utilizing a steam co-feed.

OBJECTS AND EMBODIMENTS

It is an object of the present invention to provide an improved process for the dehydrogenation of dehydrogenatable hydrocarbons and especially for the dehydrogenation of $C_2$–$C_{15}$ hydrocarbons.

Accordingly in a broad embodiment, the present invention is a dehydrogenation process comprising contacting a hydrocarbon feedstock in a dehydrogenation reaction zone with a dehydrogenation catalyst at dehydrogenation conditions and recovering the products therefrom. The dehydrogenation catalyst used in the process comprises an inorganic oxide carrier, a platinum group metal component; a first modifier component selected from the group scandium, yttrium, lanthanum, and actinium; a second modifier component selected from the group tin, lead, and germanium; and a halogen component. The process occurs preferably in the presence of a co-feed comprising steam, air, hydrogen, inert gases, or mixtures thereof.

In an alternative embodiment, the invention is a process for the dehydrogenation of $C_2$–$C_{15}$ hydrocarbons. The process consists of contacting the $C_2$–$C_{15}$ hydrocarbons along with a co-feed of steam and hydrogen in a dehydrogenation reaction zone operating at dehydrogenation reaction conditions and containing a dehydrogenation catalyst. The dehydrogenation reaction conditions include a temperature of from 400° to 900° C., a pressure of from 0.1 to 20 atmospheres, and a liquid hourly space velocity of from 1 to 100 $hr^{-1}$. The dehydrogenation catalyst preferably comprises from 0.1 to 1 wt. % platinum, from 0.1 to 2.5 wt. % yttrium, from 0.1 to 2.5 wt. % tin, from 0.1 to 15 wt. % of a third modifier component selected from Group IA or IIA of the Periodic Table of the Elements, and from 0.01 to 3 wt. % of a halogen component. The dehydrogenated product of the reaction zone is subsequently recovered.

In a narrower embodiment, the preferred hydrocarbon feedstock to the dehydrogenation process is a $C_2$–$C_6$ normal or isoparaffinic hydrocarbon. In addition, air, hydrogen, inert gases, and mixtures thereof may also be included as a co-feed to the process of this invention. Finally, the process of this invention may take place in a single reaction zone or multiple reaction zones.

DETAILED DESCRIPTION OF THE INVENTION

To summarize, the present invention is a process for the selective steam dehydrogenation of a dehydrogenatable hydrocarbon which is accomplished utilizing a single catalyst. The catalyst most useful in the process of the present invention is comprised of a platinum group metal component; a component selected from the group scandium, yttrium, lanthanum, and actinium; a component selected from the group tin, lead, and germanium; a halogen component; and an optional Group IA or IIA component from the Periodic Table of the Elements. Such a process utilizing the catalyst disclosed herein results in a dehydrogenation process with superior conversion stability in comparison to prior art catalysts and processes.

As indicated above, one feature of the catalytic composite of the process of this invention is a platinum group metal component. The platinum group metal may be selected from the group consisting of platinum, palladium, iridium, rhodium, osmium, ruthenium, or mixtures thereof. Platinum or palladium are, however, the preferred platinum group metal components. It is believed that substantially all of the platinum group metal components exists within the catalyst in the elemental metallic state.

The platinum group metal component generally will comprise about 0.01 to 10 wt. %, calculated on an elemental basis, of the final catalytic composite. Preferably, the catalyst comprises about 0.01 to 5 wt. % of the platinum group metal component, especially about 0.1 to about 1 wt. % platinum component.

The platinum group metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are or have been incorporated into the catalyst. The preferred method of incorporating the platinum group metal component is to impregnate the refractory oxide support with a solution or suspension of a decomposable compound of a platinum group metal. For example, platinum may be added to the support by commingling the latter with an aqueous solution of chloroplatinic acid. Another acid, for example, nitric acid or other catalytic components may be added to the impregnating solution to further assist in dispersing or fixing the platinum group metal component in the final catalyst composite. The platinum group metal component may be located upon the catalyst in a variety of useful manners known in the art including uniformly dispersed, surface-impregnated or surface concentrated among others.

A first modifier component selected from the group of elements consisting of scandium, yttrium, lanthanum, and actinium is also incorporated into the catalyst of the process of this invention. Preferably, the first modifier component is uniformly distributed throughout the catalyst particle. However, it is anticipated that the catalyst could be surface impregnated with the second component or any other component of the catalyst of the dehydrogenation process. The first modifier component may be present in the dehydrogenation catalyst composite in a catalytically effective amount ranging from 0.1 to 20 wt. % although a range of from 0.1 to 2.5 wt. % is preferred. The preferred second component is yttrium.

The first modifier component may be incorporated into the catalyst base by any method known in the art such as coprecipitation, cogelation, ion exchange, impregnation, or deposition from a vapor or solid source. The preferred method of incorporating the first modifier component onto the catalyst base is by impregnation with a solution or suspension of a decomposable compound of a component selected from the group scandium, yttrium, lanthanum, and actinium. The preferred impregnation may occur before, at the same time as, or before or after the addition of the other catalytic components to the catalyst base.

In another preferred method, the first modifier component may be incorporated into the catalyst base by cogelation. For example, yttrium in the form of yttrium nitrate is added to an aluminum chloride (Al sol) solution and then dropped into hot oil at about 100° C. to form a yttrium-containing spherical alumina catalyst. A similar result may be obtained by adding a yttrium or like metal solution to an alumina dough prior to extrusion to form a yttrium-containing alumina extrudate.

A second modifier component selected from the group tin, lead, and germanium is also incorporated into the catalyst of the instant dehydrogenation process. Like the platinum group metal component and the first modifier component, the second modifier component may be incorporated onto the catalyst base by any method known in the art to result in a third component that is uniformly or non-uniformly impregnated upon or within the catalyst base.

The second modifier component may be present in the dehydrogenation catalyst in a catalytically effective amount ranging from 0.01 to 5 wt. %. It is preferred that the second modifier component be present in the catalyst in an amount ranging from 0.1 to 3.0 wt. %. Finally, it is preferred that the second modifier component is tin. Examples of preferred methods of incorporating the tin component into the catalyst of the instant invention includes impregnation and cogelation. To impregnate the catalyst base with the third component, the catalyst base, preferably calcined, is contacted with a decomposable solution containing either lead, tin, or germanium. An example of such a solution would be tin nitrate. The solution is then slowly evaporated until the catalyst base comprising a third catalytic component remains. Adding the second modifier component to the catalyst by cogelation would involve a method identical to that described above for incorporating yttrium into a spherical alumina catalyst by cogelation or by extrusion.

The catalyst of the process of this invention will also comprise a halogen component. Suitable halogen components include fluorine, chlorine, bromine, and iodine. The halogen component may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound or solution containing the halogen before or after other catalyst components are incorporated with the carrier material. Suitable compounds containing the halogen include acids containing the halogen, for example, hydrochloric acid. Alternatively, the halogen component or a portion thereof may be incorporated by contacting the catalyst with a compound or solution containing the halogen in a subsequent catalyst regeneration step. In the regeneration step, carbon deposited on the catalyst as coke during use of the catalyst in a hydrocarbon conversion process is burned off the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process.

The halogen component may be present in the catalyst in an amount ranging from 0.01 to 3.0 wt. % and preferably in an amount ranging from 0.01 to 2.0 wt. %.

Because the instant process is a steam dehydrogenation process, it is anticipated that the steam will strip much of the halogen component from the catalyst. So even if the catalyst is manufactured with 2 wt. % of a halogen, the effective amount of halogen on the catalyst will most likely drop to below 0.3 wt. % soon after initial operation of the steam dehydrogenation process.

Finally, the catalyst of the instant process may comprise a third modifier component selected from Group IA and/or IIA of the Periodic Table of the Elements. These elements are lithium, sodium, potassium, rubidium, cesium, francium, beryllium, magnesium, calcium, strontium, barium, and radium.

Preferably, the Group IA or IIA component is well dispersed throughout the catalytic composite. The Group IA or IIA component generally will comprise about 0.01 to 20 wt. %, calculated on an elemental basis of the final catalytic composite. The Group IA or IIA component is preferably present in an amount ranging from 0.1 to 5 wt. % of the catalytic composite.

The Group IA or IIA component may be incorporated in the catalytic composite in any suitable manner such as, for example, by coprecipitation or cogelation, by ion exchange or impregnation, or by like procedures either before, while, or after other catalytic components are incorporated into the catalyst composition. A preferred method of incorporating the preferred Group IA and IIA components is to impregnate the carrier material with a solution of a decomposable compound of a Group IA or IIA component. In a most preferred embodiment, the Group IA or IIA component is present in the catalytic composite in an amount ranging from 0.1 to 2 wt. %.

The inorganic oxide carrier material useful for the catalyst of this process may be any carrier material known which is useful as a catalytic support. However, alumina is the most preferred support material. The most preferred inorganic oxide support of the present invention is alumina having a surface area of from 1 to 500 m$^2$/g. The alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16-inch in diameter, though particles as small as about 1/32-inch and smaller, may also be utilized, as well as particles larger than 1/16-inch diameter.

In a most preferred method, the alumina is in the form of spheres. To make alumina spheres, aluminum metal is converted into an alumina sol by reacting it with a suitable peptizing acid and water, and then dropping a mixture of the sol, and a gelling agent into a hot oil bath. The mixture forms spherical particles of an alumina gel in the hot oil bath which are easily converted into the preferred gamma- or eta-alumina carrier material by known methods including aging, drying, and calcining. Other shapes of the alumina carrier material may also be prepared by conventional methods. Any or all catalytic components previously mentioned may be added to the alumina sol or alumina carrier material prior to substrate formation.

The catalyst previously described is useful in the steam dehydrogenation process of the instant invention. Any dehydrogenatable hydrocarbon may be utilized as feed to the present invention. However, it is preferred that the hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 2 to 15 or more carbon atoms to the corresponding diolefins or acetylene derivatives. The catalyst is most useful in the dehydrogenation of $C_2$–$C_6$ paraffins into monoolefins and especially $C_3$ and $C_4$ paraffins and isoparaffins.

The dehydrogenation of a dehydrogenatable hydrocarbon such as, for example, those mentioned above, is effected in the instant process by contacting the dehydrogenatable hydrocarbon and steam, with the previously described catalyst at conditions useful for the steam dehydrogenation of hydrocarbons. Such conditions comprise temperatures which range from about 400° to about 900° C., preferably from 450° to 700° C., and a reaction pressure in the range of from about 0.1 to about 40 atmospheres, preferably from 1 to 20 atmospheres. The exact dehydrogenation conditions are, however, a function of the particular dehydrogenatable hydrocarbon undergoing dehydrogenation. Other reaction conditions will include a liquid hourly space velocity based on the total hydrocarbon charge rate of from about 0.1 to about 100 hr$^{-1}$ and steam-to-hydrocarbon molar ratios ranging from about 0.1:1 to about 40:1.

Steam is a critical feed component to the process of the present invention. Steam addition to the reaction zone has been found to dramatically improve the life of the catalyst of this process by significantly attenuating the coking tendency of the catalyst.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. In an improvement, processes have been developed which utilized a two-catalyst system with distinct beds or reactors of dehydrogenation and selective oxidation catalysts. The purpose of the selective oxidation catalysts is to selectively oxidize the hydrogen produced as a result of the dehydrogenation reaction with oxygen that had been added to the oxidation zone to generate heat internally in the process. The heat generated would typically be sufficient to cause the reaction mixture to reach desired dehydrogenation temperatures for the next dehydrogenation step. The instant invention may be accomplished in such a reactor system. However, even in such a reactor system, the addition of steam is still desirable to maintain process efficiency by providing heat and reducing catalyst coking tendencies.

According to the unique process of the present invention, a mixture of dehydrogenatable hydrocarbons, steam, and optionally a co-feed consisting of an oxygen-containing gas such as air, or hydrogen, or carbon dioxide or an inert gas or mixtures thereof are contacted with the catalytic composite of the present invention in a steam dehydrogenation reaction zone maintained at steam dehydrogenation conditions. This contacting step may be accomplished by using the catalyst in a fixed bed system, a moving bed system, a fluidized bed system, or in a batch type operation. However, in view of the fact that the attrition losses of the valuable catalyst should be minimized and of the well known operational advantages, it is preferred to use either a fixed bed catalytic system, or a dense phase moving bed system such as is shown in U.S. Pat. No. 3,725,249.

If a fixed bed catalytic reaction system is used for the process of the present invention, it is anticipated that the reaction system could take many forms. The first possibility is that the reaction would comprise a single reaction zone within a single reactor with single inlet and outlet ports. The feed hydrocarbon, steam, and any and all co-feeds would enter the inlet of the reactor and products and by-products would leave the system through the reactor outlet port. It is, of course, understood that the dehydrogenation reaction zone may be two or more distinct catalyst containing zones with suitable heating or cooling means therebetween to assure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, admixed liquid-vapor phase, or a vapor phase when they contact the catalyst, with the best results obtained in the vapor phase. The dehydrogenation reaction system then preferably comprises a dehydrogenation reaction step containing one or more fixed or dense-phase moving beds of the above-described catalytic composite. If the catalyst is located in two or more distinct catalyst beds, the co-feed may be introduced into the reaction zone at the inlet to any catalyst zone or divided among the inlets to each catalyst zone. Finally, if a co-feed is used, the molar ratio of the steam plus co-feed (to the hydrocarbon feed) will range from 0.1:1 to 40:1.

The effluent stream from the dehydrogenation zone generally will contain unconverted dehydrogenatable hydrocarbons, hydrogen and the products of dehydrogenation reactions. This effluent stream is typically cooled and passed to a hydrogen separation step to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation step. Products of the dehydrogenation reactions are recovered as final products or as intermediate products in the preparation of other compounds.

It is an aspect of this invention that the selective steam dehydrogenation conversion process be a complete process. That is to say, the process will comprise a reaction section and other sections such as gas recycle, liquid recycle, product recovery, and the like such that the process is viable and efficient. Examples of some of the product recovery techniques that could be employed alone or in combination in the product recovery zone of a hydrocarbon conversion process are: distillation including vacuum, atmospheric, and superatmospheric distillation; extraction techniques including, for example, liquid/liquid extractions, vapor/liquid extractions, supercritical extractions and other; absorption techniques, adsorption techniques, and any other known mass transfer techniques which can achieve the recovery of the desired products.

The following examples are introduced to further describe the catalyst and process of the invention. The examples are intended as illustrative embodiments and should not be considered to restrict the otherwise broad interpretation of the invention as set forth in the claims appended hereto.

EXAMPLE I

In this example, Catalyst A not of this invention was prepared by the following method. A 600 cc aluminum chloride (Al sol) tin chloride solution mixture was prepared and dropped into a 100° C. oil bath to produce 1/16-inch spherical catalyst particles. The spheres were then aged 19 hours at 100° C. and then ammonia aged at 95° C. for 6 hours using a solution prepared from 600 cc of concentrated $NH_4OH$, 900 g $NH_4Cl$, and 19 l of water. The catalyst was then water washed for 12 hours at 95° C. with a solution of 25 cc $NH_4OH$ in 19 l of water. The washed spheres were dried in air for 2 hours at 120° C. followed by calcination in air for 2 hours at 538° C.

The calcined catalyst was then impregnated with a chloroplatinic acid solution comprising 2 wt. % concentrated HCl and enough chloroplatinic acid to result in the finished base comprising 0.75 wt. % Pt. The support was evaporated to dryness and then steam stripped for 6 hours at 538° C. to reduce the catalyst chloride level to below 0.2 wt. %. The final catalyst comprised 0.75 wt. % platinum, 0.5 wt. % tin, and less than 0.2 wt. % chloride on a 1/16-inch spherical alumina base.

EXAMPLE II

Catalyst B, a catalyst of the steam dehydrogenation process of this invention was prepared as set forth below. A 600 cc mixture of aluminum chloride (Al sol) and yttrium nitrate was dropped into an oil bath operating at 100° C. The spheres were aged, washed, dried, and calcined as set forth in Example I. The calcined support comprising yttrium was then exposed to the same platinum impregnation step and chloride removal step as described in Example I followed by impregnation with a tin chloride solution after which the catalyst was evaporated to dryness and calcined at 538° C. Catalyst B comprises 0.75 wt. % platinum, 0.5 wt. % tin, and 0.89 wt. % yttrium, all on a 1/16-inch spherical alumina support.

EXAMPLE III

The catalyst of Example II was further modified with cesium in this example to produce Catalyst C. Catalyst B of Example II was contacted with a cesium nitrate solution after which the catalyst was evaporated to dryness and calcined at 538° C. Catalyst C comprises 0.75 wt. % platinum, 0.5 wt. % tin, 0.90 wt. % yttrium, and 3.2 wt. % cesium.

EXAMPLE IV

Catalysts A, B, and C were evaluated in a pilot plant for their ability to dehydrogenate propane. The charge stock is passed into a reactor containing the catalyst being tested. The effluent from the reaction zone was then analyzed to determine the amount of propane converted to propylene. The propane was fed to the reactor at a liquid hourly space velocity of 4 $hr^{-1}$. The steam-to-hydrocarbon molar feed ratio was 10 for all tests. The reactor temperature was 580° C. while the reactor pressure was maintained at 10.2 atmospheres.

A comparison of the results of the pilot plant tests of Catalysts A, B, and C can be found in Table 1.

TABLE 1

| Hours On-Stream | Propane Conversion (mole %) Catalyst | | | Propylene Selectivity (mole %) Catalyst | | |
|---|---|---|---|---|---|---|
| | A | B | C | A | B | C |
| 10 | 28 | 25.5 | 22 | 65 | 72 | 88 |
| 20 | 25 | 25 | 20 | 79 | 80 | 85 |
| 30 | 18 | 25 | 20 | 83 | 84 | 85 |
| 40 | 14 | 25 | 20 | 85 | 86 | 85 |
| 50 | 10 | 25 | 20 | 79 | 90 | 83 |
| 60 | 7 | — | — | 72 | — | — |

From Table 1, it can be seen that a steam dehydrogenation process operating with Catalysts B and C of this invention exhibit superior propane conversion and propylene selectivity in comparison to Catalyst A of the prior art.

EXAMPLE V

The steam co-feed to the pilot plant of Example IV was discontinued after about 46 hours of testing Catalyst C. The $C_3$ conversion immediately increased to 100% while the propylene selectivity dropped to below 40%. Eight hours after discontinuing the steam co-feed, the reactor became plugged with coke and the run had to be aborted.

These dramatic observations are indicative of the necessity of a steam co-feed into a dehydrogenation process of this invention using the specific catalyst herein described as useful in the instant process.

What is claimed is:

1. A process for dehydrogenating dehydrogenatable hydrocarbons by contacting a feedstock comprising dehydrogenatable hydrocarbons and steam at dehydrogenation conditions, with a dehydrogenation catalyst comprising an inorganic oxide carrier and catalytically effective amounts of a platinum group component, a first modifier component selected from the group scandium, yttrium, and actinium, a second modifier component selected from the group tin, lead, and germanium, and a halogen component and recovering the products of the process.

2. The process of claim 1 further characterized in that the dehydrogenatable hydrocarbon is a $C_2$-$C_{15}$ normal or isoparaffin, naphthene, or alkylaromatic.

3. The process of claim 1 further characterized in that the dehydrogenation conditions include a temperature of from 400° to 900° C., a pressure of from 0.1 to 40 atmospheres, a liquid hourly space velocity of from 0.1 to 100 hr$^{-1}$, and a steam-to-hydrocarbon molar feed ratio of from 0.1:1 to 40:1.

4. The process of claim 1 further characterized in that the dehydrogenation catalyst comprises an inorganic oxide carrier and
   (a) from 0.01 to 5 wt. % of a platinum group metal component,
   (b) from 0.1 to 20 wt. % of the first modifier component selected from the Group scandium, yttrium, or actinium,
   (c) from 0.01 to 5 wt. % of the second modifier component selected from the group tin, germanium, or lead, and
   (d) from 0.01 to 2 wt. % of a halogen component, said percentages based upon the weight of the elemental metals as a portion of the overall catalyst weight.

5. The process of claim 4 further characterized in that the platinum group metal component is platinum and that the first and second modifier components are yttrium and tin, respectively.

6. The process of claim 5 further characterized in that hydrogen, air, inert gases, or mixtures thereof are included as a portion of the feed to the dehydrogenation reaction zone.

7. A process for dehydrogenating $C_2$-$C_{14}$ normal and isoparaffins by contacting the $C_2$-$C_{14}$ normal and isoparaffins and steam at a temperature of from 500° to 700° C. and a pressure of from 1 to 20 atmospheres with a dehydrogenation catalyst comprising inorganic oxide carrier and
   (a) from 0.1 to 1 wt. % of a platinum group component,
   (b) from 0.1 to 2.5 wt. % of the first modifier component, yttrium,
   (c) from 0.1 to 2.5 wt. % of the second modifier component, tin,
   (d) from 0.1 to 5 wt. % of a third modifier component selected from Group IA or IIA of the Periodic Table of the Elements, and
   (e) from 0.01 to 0.3 wt. % of a halogen component, and recovering the reaction products therefrom.

8. The process of claim 7 further characterized in that the refractory oxide carrier is alumina.

9. The process of claim 8 further characterized in that a co-feed consisting of hydrogen, air, or an inert gas, or mixtures thereof is included as a portion of the feed to the dehydrogenation reaction zone.

10. The process of claim 9 further characterized in that the dehydrogenation reaction zone consists of two or more distinct catalyst containing zones.

11. The process of claim 9 further characterized in that the dehydrogenation reaction zone hydrocarbon feed comprises $C_3$ and $C_4$ paraffins and isoparaffins.

12. A process for the dehydrogenation of $C_2$-$C_5$ normal and isoparaffins comprising contacting the $C_2$-$C_5$ normal and isoparaffins and a co-feed of steam at dehydrogenation reaction conditions including a temperature of from 400° to 900° C., a pressure of from 0.1 to 20 atmospheres, and a liquid hourly space velocity of from 1 to 10 hr$^{-1}$ with a dehydrogenation catalyst comprising
   (a) from 0.1 to 1 wt. % platinum,
   (b) from 0.1 to 2.5 wt. % yttrium,
   (c) from 0.1 to 2.5 wt. % tin,
   (d) from 0.1 to 2 wt. % of a Group IA or IIA component, and
   (e) less than 0.25 wt. % chloride, and recovering the dehydrogenation reaction products.

13. The process of claim 12 further characterized in that the co-feed comprising steam and hydrogen is introduced into the dehydrogenation reaction at a molar ratio of steam and hydrogen to hydrocarbon feed ranging from 0.1:1 to 40:1.

14. The process of claim 13 further characterized in that the Group IA of IIA component is cesium.

15. The process of claim 13 further characterized in that air is a co-feed to the dehydrogenation reaction zone.

16. The process of claim 13 further characterized in that the dehydrogenation reaction zone consists of two or more distinct catalyst containing zones with a portion to all of the co-feed being introduced to the process between the distinct catalyst containing zones.

* * * * *